US00PP29792P2

(12) United States Plant Patent
Reisch et al.

(10) Patent No.: US PP29,792 P2
(45) Date of Patent: Nov. 6, 2018

(54) SEEDLESS TABLE GRAPE NAMED 'NY98.0228.02'

(50) Latin Name: ***Vitis* sp. (interspecific hybrid)**
Varietal Denomination: NY98.0228.02

(71) Applicant: Cornell University, Ithaca, NY (US)

(72) Inventors: Bruce Reisch, Geneva, NY (US); R. Stephen Luce, Ovid, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/732,418

(22) Filed: Nov. 7, 2017

(51) Int. Cl.
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — Morrison & Foerster LLP

(57) ABSTRACT

A new and distinct cultivar of seedless table grape (*Vitis* sp.) named 'NY98.0228.02' is described. This new and distinct cultivar is particularly characterized by its large berry size, seedlessness, and berry flavor.

4 Drawing Sheets

Botanical classification: *Vitis* sp. (interspecific hybrid).

Varietal denomination: The varietal denomination of the claimed seedless table grape cultivar is 'NY98.0228.02'.

BACKGROUND OF THE INVENTION

Grapes are produced on deciduous lianas of the botanical genus *Vitis*. Grapes can be consumed as fresh fruit (i.e., table grapes) or they can be processed into wine, jam, juice, jelly, grape seed extract, raisins, vinegar, and grape seed oil. Grapes may also be dried to produce raisins. Grape clusters can include from about 15 to over 300 berries, and fruit color can vary greatly (e.g., crimson, black, dark blue, yellow, green, orange and pink). Anthocyanins and other pigments are responsible for the varying shades of purple in red wines. Berry shapes may vary from round or ellipsoid to oval or falcoid.

Most grapes come from cultivars of *Vitis vinifera*, the European grapevine that is native to the Mediterranean and Central Asia. Some fruit are also produced from additional species, and many species have been hybridized with *V. vinifera* to create a range of wine and table grapes, as well as rootstock vines.

Table grapes are grapes intended for consumption while they are fresh, and consumers have a strong preference for seedless grapes. Grape cultivars that are the most commonly sold as table grapes include Sultana (Thompson Seedless), Flame, Ruby Seedless, Sugraone, and Concord. Table grape cultivars generally have lower sugar and acidity than wine grapes and may be more flavorful when eaten.

Table grapes are an important and valuable fruit crop, and there is desire for table grapes that can be grown at home. Accordingly, there is a need for new grapevine cultivars that produce table grapes. In particular, there is a need for improved grapevine cultivars that are well-adapted to cold winters, short growing seasons, and the diseases prevalent in cool climates.

BRIEF SUMMARY OF THE INVENTION

In order to meet these needs, the present invention is directed to an improved cultivar of table grape. In particular, the invention relates to a new and distinct seedless table grape (*Vitis* sp.) denominated as 'NY98.0228.02', which was developed by a breeding program in Geneva, N.Y. This new and distinct table grape cultivar was a result of hybridization followed by selection and asexual reproduction of an elite seedling that was particularly characterized by its large berry size, small, soft seed traces, and fruity flavor.

Cultivation Summary

The seedless table grape cultivar 'NY98.0228.02' is a hybrid originated from controlled pollination cross in June of 1998 in Geneva, N.Y., between the proprietary female parent selection 'NY87.0439.02' (unpatented) and the proprietary male parent selection 'NY88.0515.01' (unpatented).

The cross was performed by emasculating the female vine prior to flowering, and applying pollen of the male vine to the bagged and protected pistils of the female vine. Seeds were then germinated in a greenhouse in spring of 1999 and this family of grapevines was grown in an irrigated field nursery in summer of 1999.

Both parental selections, as well as the new seedless table grape cultivar 'NY98.0228.02', are tetraploids with 76 chromosomes, as opposed to 38 chromosomes for common table grape cultivars.

From the original cross in 1998, 87 seedling grapevines were germinated from seeds of the cross in a greenhouse beginning March of 1999, and then grown in a nursery from June to October of 1999 in Geneva, N.Y. These seedlings were then planted in May of 2000 to a permanent vineyard site. The original vine of seedless table grape cultivar 'NY98.0228.02' was planted in Geneva, N.Y. Fruit production was first observed in 2002 and, after fruiting again in 2003, the vine was first asexually propagated in a nursery in the spring of 2004. After hardening under field conditions, vines of 'NY98.0228.02' were stored under moist and cold (under 5° C.) conditions until planting in spring. Six vines were planted to a location on the same farm in May of 2005 in Geneva, N.Y., and bore fruit in 2006. An additional three vines were asexually propagated and planted on May 7 of 2014 in Geneva, N.Y.

The present invention relates to a new and distinct cultivar of seedless table grape named 'NY98.0228.02', characterized by its large and very productive vines with moderate disease resistance, large clusters of moderately large blue seedless slipskin (pulp does not adhere to the flesh) berries that are soft, juicy and flavorful, and a maturity of early to mid-season. 'NY98.0228.02' was selected for its large berry size, seedlessness, and flavor.

Distinguishing Characteristics

Female Parent is Breeding Program Selection—'NY87.0439.02'

Seedless table grape cultivar 'NY98.0228.02' is distinguished from female parent selection 'NY87.0439.02' by the following unique combination of characteristics: 'NY98.0228.02' is seedless with small rudimentary seed traces, whereas 'NY87.0439.02' is fully seeded.

Male Parent is Breeding Program Selection—'NY88.0515.01'

Seedless table grape cultivar 'NY98.0228.02' is distinguished from male parent selection 'NY88.0515.01' by the following unique combination of characteristics: 'NY98.0228.02' produces larger berries and larger clusters than does 'NY88.0515.01', whereas both are seedless blue grapes.

Comparison of 'NY98.0228.02' with 'Concord' and 'Concord Seedless'

Seedless table grape cultivar 'NY98.0228.02' is distinguished from 'Concord' (unpatented) and 'Concord Seedless' (unpatented) and other table grape cultivars by the following unique combination of characteristics: very large berries, large clusters, cold hardiness suitable for USDA Zone 5, with small and soft seed traces. The flavor of 'NY98.0228.02' berries is similar to that of 'Concord' and 'Concord Seedless', but the berries of 'NY98.0228.02' are much larger than both 'Concord' and 'Concord Seedless'. In addition, 'Concord Seedless' produces small berries borne on small clusters, and the seed remnant is sometimes hardened and noticeable when eaten, whereas the seed trace of 'NY98.0228.02' is much less noticeable.

Stability

Seedless table grape cultivar 'NY98.0228.02' has been propagated from both hardwood cuttings and via bench grafting onto rootstock 'Couderc 3309' (unpatented). Asexual reproduction of 'NY98.0228.02' by hardwood cuttings and grafting onto rootstocks shows that the foregoing and all other characteristics and distinctions come true to form and are established and transmitted through succeeding propagations.

BRIEF DESCRIPTION OF THE DRAWINGS

Seedless table grape cultivar 'NY98.0228.02' is illustrated by the accompanying photographs. The colors shown are as true as can be reasonably obtained by conventional photographic procedures. However, the colors in the photograph may vary with lighting conditions and, therefore, color characteristics of this new cultivar should be determined with reference to the observations described herein, rather than from the photographs alone. The photographs are obtained from grapevines that are 13 years old.

DETAILED BOTANICAL DESCRIPTION

Figure 1:
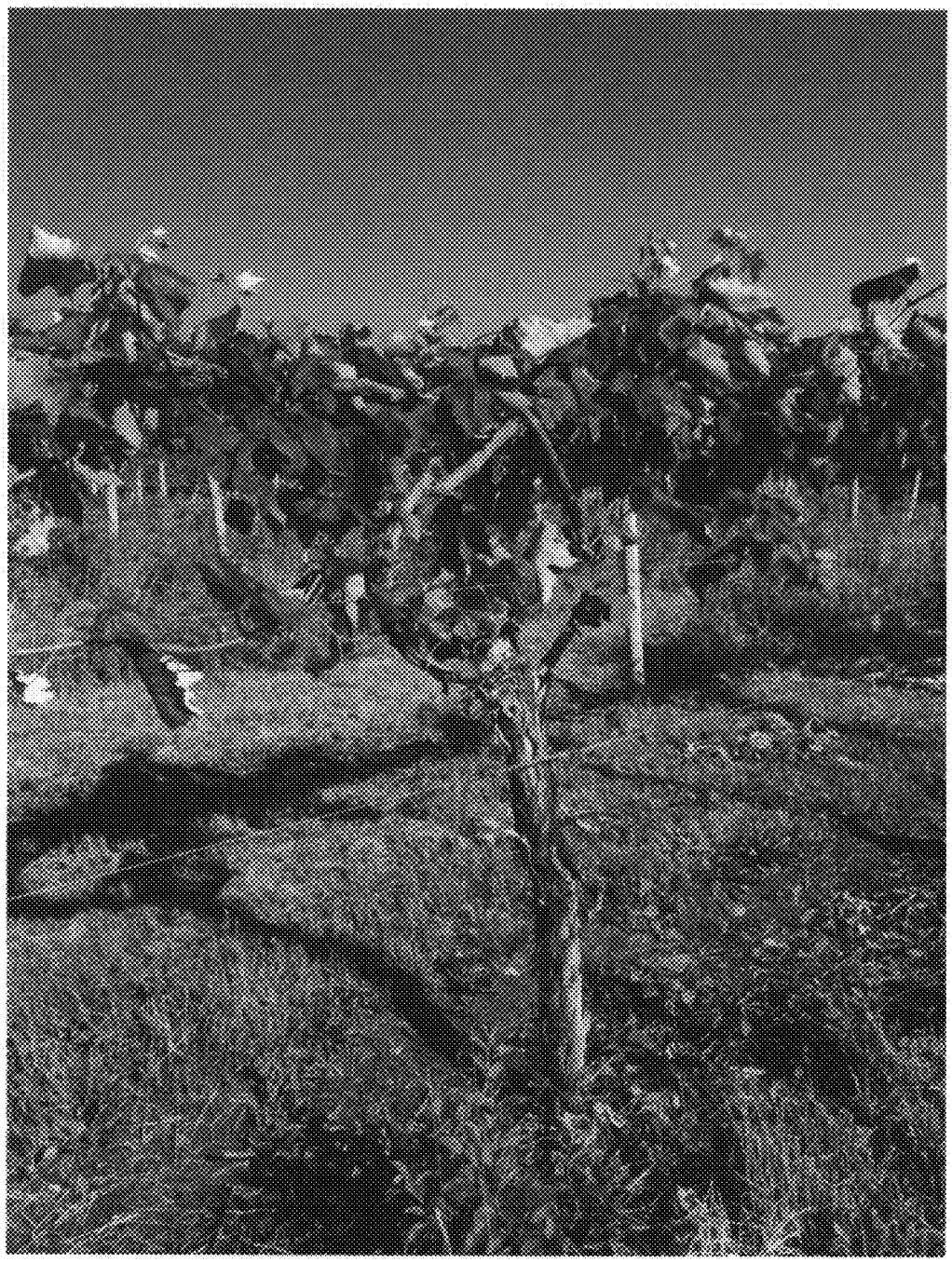
FIG. 1 is a photograph depicting a vine of 'NY98.0228.02'.
Figure 2:
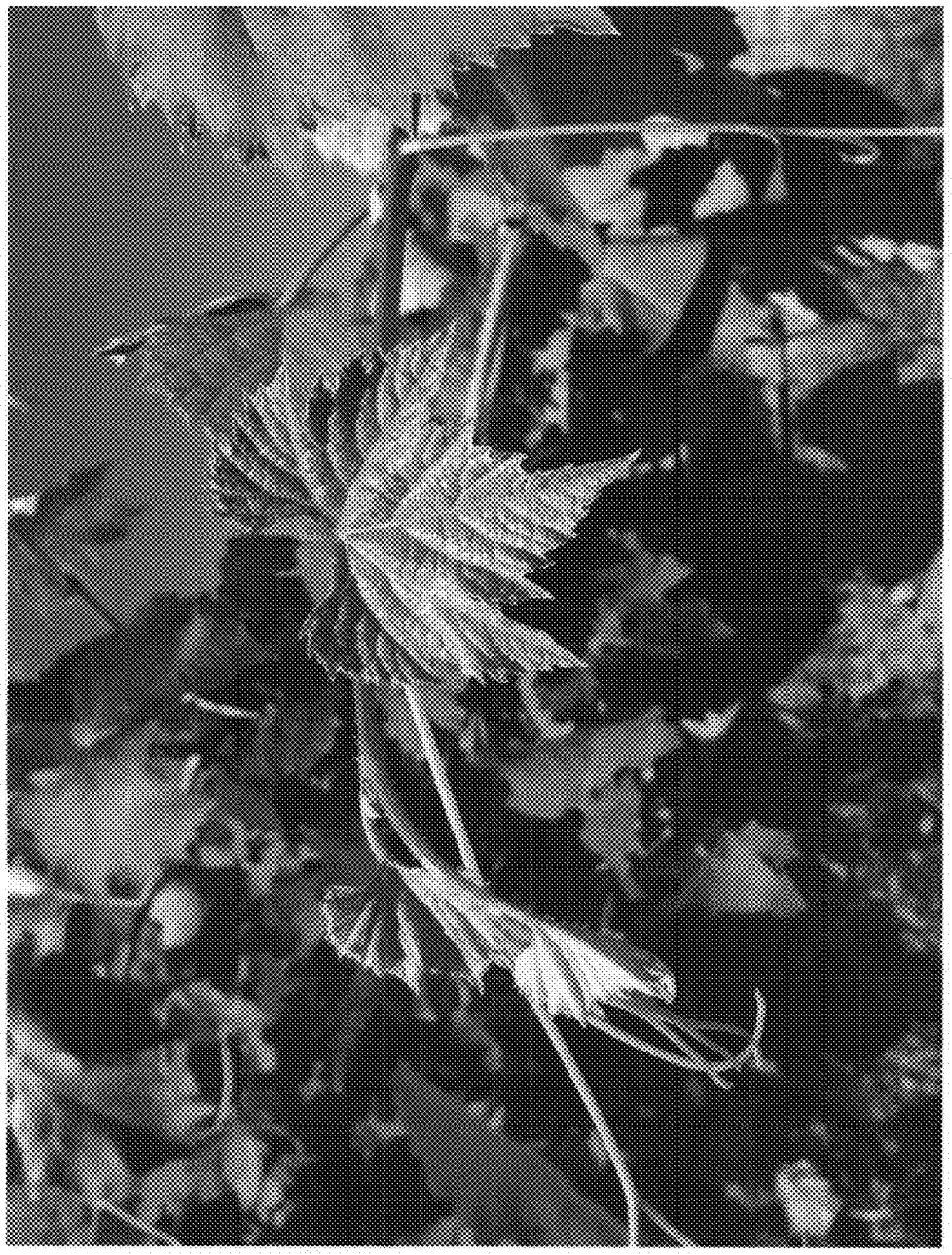
FIG. 2 is a photograph depicting a young shoot of 'NY98.0228.02'.
Figure 3:
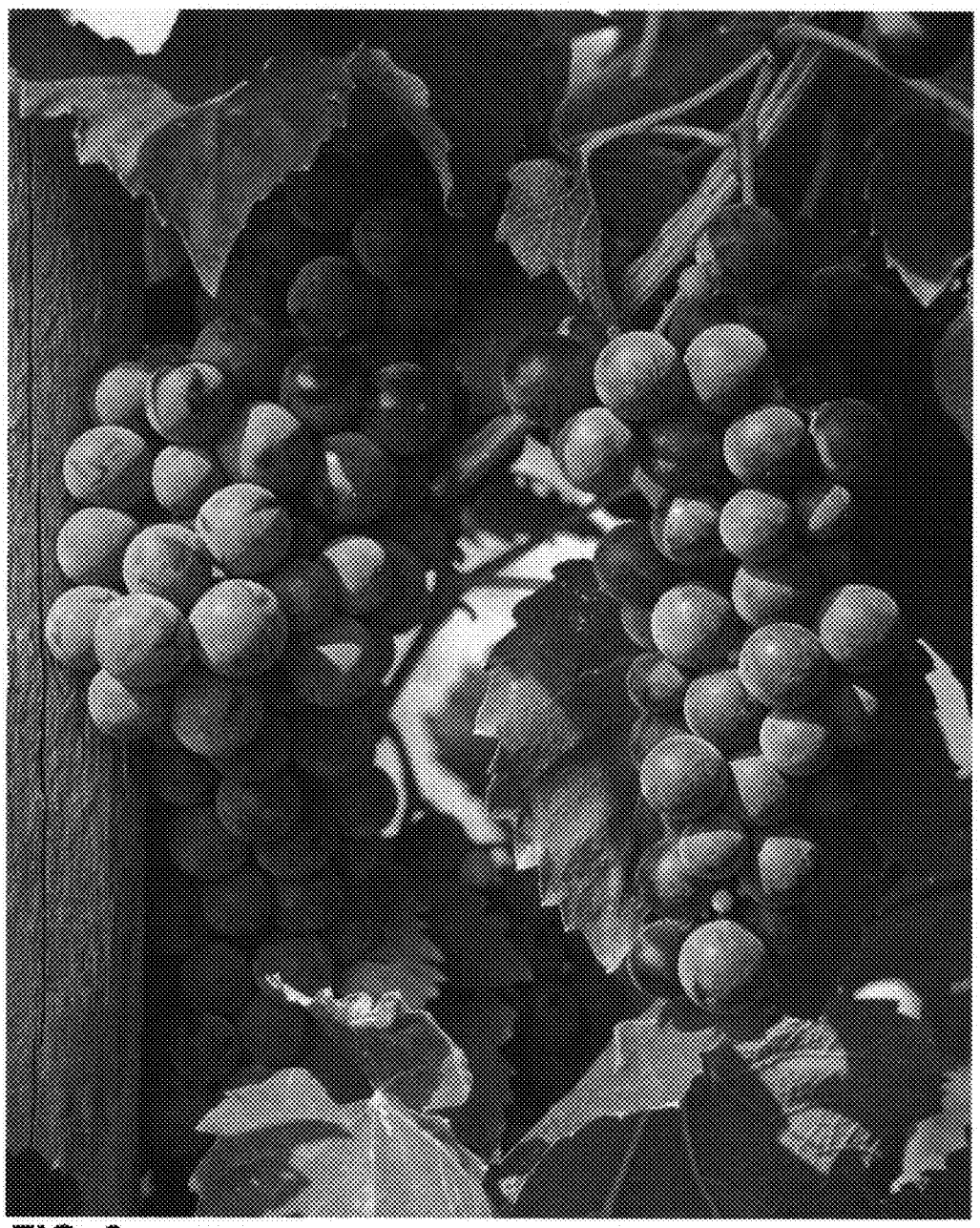
FIG. 3 is a photograph depicting fruit clusters of 'NY98.0228.02'.
Figure 4:
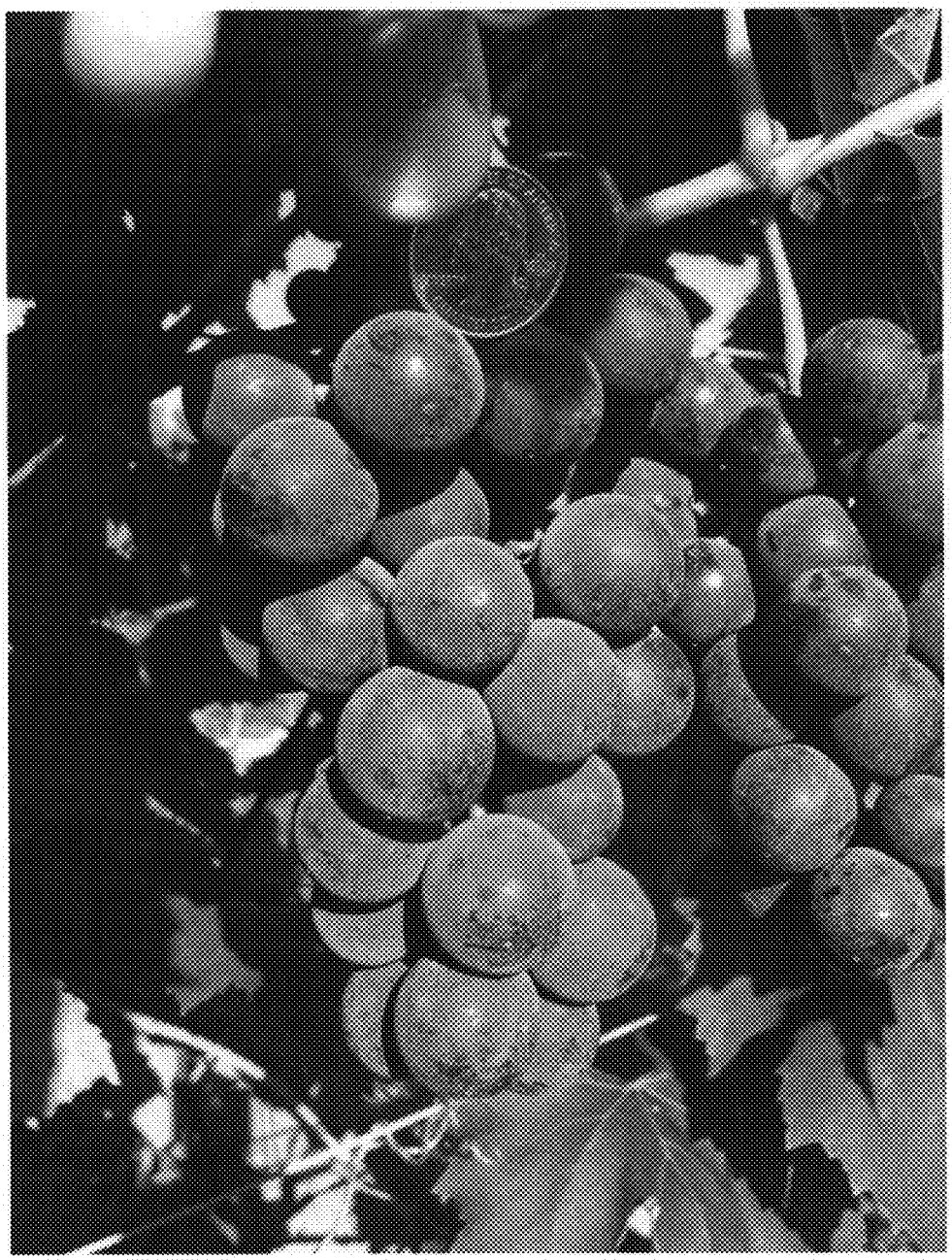
FIG. 4 is a photograph depicting a fruit cluster of 'NY98.0228.02' with a U.S. quarter dollar coin as a size reference (approximately 24 mm in diameter).

The following description sets forth the distinctive characteristics of seedless table grape cultivar 'NY98.0228.02'. The following description is based on the originally identified grapevine and asexually reproduced progeny, grown in Geneva, N.Y.

Referring more specifically to the details of the new and distinct cultivar of table grape, unless otherwise specified, measurements were taken on vines that were 13 years of age in Geneva, N.Y. Numbers provided are averages of data measured from the sampling of vines.

Certain characteristics of this cultivar may change with changing environmental conditions (e.g., light, temperature, moisture, etc.), nutrient availability, or other factors. Quantified measurements are expressed as an average of measurements taken from a number of individual plants of the new cultivar. The measurements of any individual plant, or any group of plants, of the new cultivar may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart, London 2001.

Vine:

*Size*.—Medium. Vine size as determined on grapevines growing on a three wire vertical trellis with the first wire set 86.4 cm above the ground; the second wire at 127 cm above the ground; and the third wire at 178 cm above the ground. The vine was trained to produce a grapevine height of 191 cm and a grapevine spread of 244 cm. Vine size as indicated by the weight of dormant prunings of canes is 0.8-1.5 kg for own-rooted vines and 1.3-2.5 kg for vines grafted on 'Couderc 3309'.

*Productivity*.—Productive. When spaced 244 cm by 274 cm, grafted vines produce 15 kg of fruit, and own-rooted vines produce 13.8 kg of fruit. In comparison, an average table grape cultivar produces approximately 7-10 kg per grapevine grown in New York.

*Regularity of bearing*.—Regular. Annual pruning of canes is required for reliable production.

Canes:

*Growth habit*.—Semi-trailing.

*Diameter*.—At internode midpoint above node 4: 7.5 mm for own-rooted vines and 9.2 mm for grafted vines.

*Internode length*.—At base between nodes 1 and 2: 2.55 cm for own-rooted vines and 2.73 cm for grafted vines; between nodes 2 and 3: 4.72 cm for own-rooted vines and 5.47 cm for grafted vines; between nodes 3 and 4: 6.86 cm for own-rooted vines and 7.29 cm for grafted vines.

*Surface texture*.—Smooth.

*Color of mature cane*.—Brown with darker longitudinal stripes. Color of the stripes is RHS 183B to RHS 183C (Greyed-purple), and the color of the background is RHS N170B to RHS N170C (Greyed-orange).

*Buds*.—Color — RHS 175A (Greyed-orange). Date of bud break — In 2017, around May 4, three days after cultivar 'Concord'.

*Young shoots*.—Surface texture — Cobwebby hairs but smooth below. Youngest leaves at tip are wooly (felty). Young shoots have felty indument. Diameter — 8 mm at base, 7 mm at midpoint and 4 mm at tip, measured when shoots are 76.2 cm in spring. Internode length — 8.5 cm at $4^{th}$ internode from base. Color — RHS 144C (Yellow-green). Shoot shape — Slightly curved.

*Shoot tip*.—Stem of shoot tip — Color: RHS 144C (Yellow-green). Some shoot tips are lightly pigmented with anthocyanins. Youngest leaf, not expanded — Color: upper surface: RHS 142B and RHS 144C (Green); lower surface: RHS N155C with whitish pubescence. Form — Open, but flattened at the very tip.

*Tendrils*.—Length — Average 20 cm (range 14-26 cm). Diameter — 2.5-3.0 mm. Shape — Both bifurcated and trifurcated, and curled on the distal end. Surface texture — Smooth with sparsely scattered dark stiff hairs. Pattern — Subcontinuous placement with series of 2, 3, or 4 tendrils in a row, followed by a node without a tendril, and starting at first node apical to clusters. Color of immature growth — RHS N144A (Yellow-green).

Leaves:

*Size*.—Large. The midvein ($L_1$) is 15.2 cm long; the distal lateral vein $L_2$ is 13.3 cm long; and the proximal lateral vein $L_3$ is 9.8 cm long. The angle between the $L_1$ and $L_3$ is 89 degrees, and between $L_1$ and the first vein off $L_3$ is 122 degrees.

*Arrangement*.—Simple and alternate.

*Length*.—Average 19.3 cm.

*Width*.—Average 19.3 cm.

*Shape*.—Cuneo-truncate (long midvein with prominent petiolar open sinus).

*Lobes*.—Number: mostly 3, sometimes 5.

*Adaxial surface of mature leaves*.—Color: RHS 137A (Green). Adaxial surface is glabrous, flat, and smooth to slightly bullate.

*Abaxial surface of mature leaves*.—Color: RHS 138B-138C (Green). Abaxial surface has short pubescent hairs.

*Veins of mature leaves*.—Color — RHS 144D (Yellow-green). Thickness — Thickness of midvein at center of leaf is 1.5 mm. Anthocyanin of main veins — None.

*Leaf margin*.—Serrated with shape of teeth mostly pointed, occasionally convex; medium in size.

*Petiole sinus*.—Mostly open lyre shaped petiolar sinus, occasionally closed. Petiolar sinus on mature leaves is 5.5 cm long (range 4-6 cm) and 2.5 cm wide at widest point (range 2-3 cm).

*Petiole*.—Length — 7.1 cm. Diameter — 3.4 mm. Surface texture — Smooth but with sparse short hairs. Several prominent longer hairs at base of petiole surrounding node. Color — RHS 144C (Yellow-green). Petiole of young leaf — Color: RHS 144C (Yellow-green).

*Shape of unfolded young leaf*.—Flat.

*Stipules*.—Color: RHS N199C (Grey brown).

Flowers:

*Size*.—Large.

*Unopened flowers*.—Diameter — 2.5 mm. Length — 4.0 mm. Surface texture — Smooth/bullate.

*Date of bloom*.—In 2017, trace bloom on June 16.

*Date of 50% bloom*.—In 2017, June 19.

*Inflorescence*.—Panicle.

*Fragrance*.—Aromatic.

*Cluster size at bloom*.—Generally medium-large.

*Pre-bloom cluster*.—Length — 14.5 cm. Width — 4.5 cm. Peduncle length — 2.5 cm. Peduncle color — RHS 145B (Yellow-green). Shape — Shouldered/Conical.

*Calyptra*.—Color: RHS 144B (Yellow-green).

*Stamens*.—5 or 6 per flower.

*Pistil*.—Well-developed, large, and prominent.

*Ovary*.—Color: RHS 144A (Yellow-green).

*Pollen*.—Normal, fertile, abundant.

*Anther*.—Color: RHS 162B (Greyed-yellow).

Clusters:

*Weight*.—Measured on pruned vines, 450 grams on grafted vines, and 270 grams on own rooted vines.

The following measurements are for basal clusters on primary shoots:

*Length*.—18.5 cm on grafted vines, and 18.3 cm on own-rooted vines.

*Width*.—12.5 cm on grafted vines, and 12.3 cm on own-rooted vines.

*Shape*.—Conical and shouldered.

*Density*.—Compact, on average 88 berries per cluster on grafted vines, and 66 berries per cluster on own-rooted vines.

*Clusters per shoot*.—2 clusters per primary shoot.

*Peduncle*.—Length — 26 mm on grafted vines and 20 mm on own-rooted vines. Diameter — 4.1 mm on grafted vines, and 4.7 mm on own-rooted vines. Color — RHS 144D (Yellow-green). Texture — Smooth, with very sparse short brown hairs.

*Pedicel*.—There is a medium attachment between the berry and the pedicel. Length — 7.9 mm on grafted vines, and 6.7 mm on own-rooted vines. Diameter — 1.9 mm on grafted vines, and 1.8 mm on own-rooted vines. Color — RHS 143C (Green).

*Brush*.—Length — 7.7 mm on grafted vines, and 9.3 mm on own-rooted vines. Color — RHS 187B (Greyed-purple).

Berry:

*Weight*.—Large. In 2016, average 5.4 grams per berry on grafted vines, and 5.3 grams per berry on own-rooted vines. In 2015, average 6.1 grams per berry on own-rooted vines. In 2014, 7.7 grams per berry on own-rooted vines.

*Berry uniformity*.—Moderately uniform in size. Own-rooted vines have small numbers of hard green shot berries.

*Berry shape*.—Spherical. 20.3 mm long and 20.0 mm wide on grafted vines; 19.5 mm long and 19.4 mm wide on own-rooted vines.

*Seeds*.—Rudimentary, small, not lignified, with stenospermocarpic seedlessness.

*Seed trace counts and weights*.—Average 1.5 seed traces per berry (same for grafted and own-rooted vines). In comparison, there are on average 2.86 traces per berry for cultivar 'Concord Seedless'. The dry weight per seed trace for 'NY98.0228.02' is 4.6 mg (on grafted vines) and 5.4 mg (on own-rooted vines).

*Berry color with waxy bloom in place*.—RHS N187B-N187C (Greyed-purple).

*Berry color with waxy bloom gently rubbed off*.—RHS N186A (Greyed-purple).

*Berry bloom*.—Moderate.

*Surface texture*.—Smooth.

*Tendency to crack*.—Slight, exacerbated by bird or insect damage.

*Berry flesh color*.—RHS 193C (Grayed-green).

*Berry texture*.—Soft and juicy.

*Flavor*.—Fruity, similar to cultivar 'Concord'.

*Soluble solids*.—In 2016, 16.0° Brix.

*Titratable acidity*.—In 2016, 6.3 g/L.

*pH*.—In 2016, 3.23.

*Ripening*.—Uniform. Ripening for harvest occurs approximately mid-September in a typical year in Geneva, N.Y.

*Use*.—Consumed fresh as table grape.

Resistance to diseases: When grown under conditions where a fungicide program was used for medium level control of the prevalent diseases, symptoms of downy mildew were rarely observed, and leaf powdery mildew was observed two months after the final fungicide application. Vines of 'NY98.0228.02' are categorized as having intermediate resistance to downy mildew (*Plasmopara viticola*) and moderate susceptibility to foliar powdery mildew (*Erisyphe necator*).

We claim:

1. A new and distinct cultivar of seedless table grape named 'NY98.0228.02' as herein described and illustrated.

* * * * *